(12) United States Patent
Merritt et al.

(10) Patent No.: US 10,766,770 B2
(45) Date of Patent: Sep. 8, 2020

(54) SYSTEMS AND METHODS OF PRODUCTION OF HYDROGEN CONTAINING COMPOUNDS USING PRODUCTS OF FUEL CELLS

(71) Applicant: GRANNUS, LLC, Tucson, AZ (US)

(72) Inventors: James Kelly Merritt, Lafayette, OR (US); Matthew Cox, Tucson, AZ (US)

(73) Assignee: GRANNUS, LLC, Tucson, AZ (US)

( * ) Notice: Subject to any disclaimer, the term of this patent is extended or adjusted under 35 U.S.C. 154(b) by 0 days.

(21) Appl. No.: 16/302,559

(22) PCT Filed: May 18, 2017

(86) PCT No.: PCT/US2017/033275
§ 371 (c)(1),
(2) Date: Nov. 16, 2018

(87) PCT Pub. No.: WO2017/201254
PCT Pub. Date: Nov. 23, 2017

(65) Prior Publication Data
US 2019/0284045 A1    Sep. 19, 2019

Related U.S. Application Data

(60) Provisional application No. 62/338,296, filed on May 18, 2016.

(51) Int. Cl.
*C01B 3/02*     (2006.01)
*C01B 3/38*     (2006.01)
(Continued)

(52) U.S. Cl.
CPC .............. *C01B 3/025* (2013.01); *C01B 3/36* (2013.01); *C01B 3/38* (2013.01); *C01B 3/50* (2013.01);
(Continued)

(58) Field of Classification Search
CPC ........... C01B 3/025; C01B 3/38; C01B 3/508; C01B 2203/147; C01B 2203/068;
(Continued)

(56) References Cited

U.S. PATENT DOCUMENTS 9,580,315 B2    2/2017    Chandran et al.
9,783,417 B2    10/2017    Chandran et al.
(Continued)

FOREIGN PATENT DOCUMENTS

WO      2013049368 A1    4/2013
WO      WO-2014001917 A2 *    1/2014

OTHER PUBLICATIONS

McLarty et al. "Poly-generating closed cathode fuel cell with carbon capture" 2014, Applied Energy ;131; 108-116 (Year: 2014).*

*Primary Examiner* — Amber R Orlando
*Assistant Examiner* — Syed T Iqbal
(74) *Attorney, Agent, or Firm* — Dentons US LLP

(57) ABSTRACT

Disclosed herein are methods and systems for the production of hydrogen-containing compounds, such as ammonia and urea from a product stream of a fuel cell unit. The production of ammonia and optionally urea can also include a net power production. Alternatively, the hydrogen stream from the fuel cell unit can be directed to the production of synthetic hydrocarbons liquids.

6 Claims, 2 Drawing Sheets

(51) Int. Cl.
  *C01B 3/50* (2006.01)
  *H01M 8/0612* (2016.01)
  *H01M 8/0668* (2016.01)
  *H01M 8/0606* (2016.01)
  *C25B 5/00* (2006.01)
  *H01M 8/04082* (2016.01)
  *C01B 3/36* (2006.01)
  *C07C 273/04* (2006.01)
  *H01M 8/04119* (2016.01)
  *C07C 1/12* (2006.01)
  *C07C 9/04* (2006.01)

(52) U.S. Cl.
  CPC ............ *C01B 3/508* (2013.01); *C07C 273/04* (2013.01); *C25B 5/00* (2013.01); *H01M 8/04164* (2013.01); *H01M 8/04201* (2013.01); *H01M 8/0606* (2013.01); *H01M 8/0618* (2013.01); *H01M 8/0668* (2013.01); *C01B 2203/042* (2013.01); *C01B 2203/043* (2013.01); *C01B 2203/0415* (2013.01); *C01B 2203/0445* (2013.01); *C01B 2203/06* (2013.01); *C01B 2203/067* (2013.01); *C01B 2203/068* (2013.01); *C01B 2203/1241* (2013.01); *C01B 2203/147* (2013.01); *C01B 2203/86* (2013.01); *C07C 1/12* (2013.01); *C07C 9/04* (2013.01); *Y02E 60/566* (2013.01)

(58) Field of Classification Search
  CPC ...... C01B 2203/0445; C01B 2203/042; C01B 2203/1241; C01B 2203/067; H01M 8/0668; H01M 8/0618; C07C 9/04; C07C 1/12
  See application file for complete search history.

(56) References Cited

U.S. PATENT DOCUMENTS

| | | |
|---|---|---|
| 9,845,240 B2 | 12/2017 | Chandran et al. |
| 10,011,482 B2 | 7/2018 | Chandran et al. |
| 10,011,483 B2 | 7/2018 | Chandran et al. |
| 10,065,858 B2 | 9/2018 | Chandran et al. |
| 10,214,418 B2 | 2/2019 | Chandran et al. |
| 10,280,081 B2 | 5/2019 | Chandran et al. |
| 2019/0210873 A1 | 7/2019 | Chandran et al. |
| 2019/0210874 A1 | 7/2019 | Chandran et al. |

* cited by examiner

SYSTEMS AND METHODS OF PRODUCTION OF HYDROGEN CONTAINING COMPOUNDS USING PRODUCTS OF FUEL CELLS

This application is a 371 National Stage application of International Application No. PCT/US2017/033275, filed May 18, 20017, which claims benefit of U.S. provisional application No. 6,233,8296, filed May 18, 2016, the entire contents of each of which are herein incorporated by reference in their entirety.

FIELD OF THE INVENTION

This invention relates to methods and systems of production of hydrogen compounds using the products of fuel cells. More specifically, the invention relates to a polygeneration process for the production of ammonia and/or nitrogen based fertilizers, or methanol from a fuel cell product stream. The invention also relates to a polygeneration process for the production of hydrocarbon liquids such as gasoline or diesel from natural gas using a fuel cell unit.

BACKGROUND OF THE INVENTION

Nitrogen is an important nutrient for supporting development and growth of plant life. Ammonia and urea are two common nitrogen containing compounds that are widely used in the fertilizer industry, as well as being used as basic chemicals in the production of a variety of different chemical compounds. Ammonia is a precursor to many nitrogen containing compounds, including urea, and therefore is an important chemical to the fertilizer industry. Ammonia is one of the most produced compounds, with a global annual production capacity of over 195 million metric tonnes. Approximately 80% or more of global production of ammonia is utilized as agricultural fertilizer. Urea, ammonium nitrate, ammonium phosphates, nitric acid, and ammonium sulfate were the major derivatives of ammonia.

Urea (or carbamide) has the highest nitrogen content of all commonly used solid nitrogenous fertilizers. Due to the wide use of urea in fertilizers as a convenient source of nitrogen, urea production is important. Additionally, urea is an important feedstock for the manufacturing of plastics, urea-formaldehylde resins, adhesives, and pharmaceuticals, and is also important as a feed product for ruminant animals.

Ammonia can be produced from different hydrocarbon feedstocks such as natural gas, coal, and oil. Natural gas accounts for more than 95% of ammonia tonnage. Generally, industrial plants producing ammonia and ammonia based fertilizers suffer from high feedstock costs, excessive energy requirements, and high emissions. Thus, a need exists for the development of new methods for the production of hydrogen compounds, such as ammonia and urea, with reduced costs and emissions.

SUMMARY

Disclosed herein are systems and methods addressing the shortcomings of the art, and may provide any number of additional or alternative advantages. The system and methods described herein provide methods and systems of production of hydrogen compounds, such as ammonia and urea, from a product stream of a fuel cell unit.

An embodiment of the invention includes a method for the production of ammonia from byproduct gases of a fuel cell process. The method includes the steps of: supplying a hydrocarbon feedstock and oxygen to a fuel cell unit to produce a first product stream containing carbon dioxide and hydrogen; supplying the gaseous product stream containing carbon dioxide and hydrogen from the fuel cell to a first condenser to remove water and produce a second product stream containing substantially pure hydrogen and carbon dioxide as compared to the first product stream; supplying the second product stream to a carbon dioxide removal unit to produce a hydrogen stream and a high purity carbon dioxide stream, the carbon dioxide stripper being charged with a solvent suitable for extracting carbon dioxide, and the hydrogen stream containing minor amounts of inert gases and carbon dioxide; supplying the hydrogen stream containing minor amounts of inert gases and carbon dioxide to a first reactor containing a first catalyst to produce a methane product stream and a high purity hydrogen stream, the first catalyst facilitating production of methane and water from the minor amounts of carbon dioxide present in the hydrogen stream; then condensing the water from the hydrogen stream; and then supplying the high purity hydrogen stream from the first reactor and nitrogen gas from an air separation unit to a second reactor containing a second catalyst to produce an ammonia product stream.

The method can alternately use a pressure swing adsorption unit, membrane separator, or mole sieve to purify the hydrogen stream, alone or in conjunction with the other treatments such as the methanator, to further purify the hydrogen prior to submitting the hydrogen to the ammonia synthesis reactor with the objective of achieving less than 50 ppm oxygen content in hydrogen admitted to the hydrogen synthesis reactor.

The method can further include supplying the high purity carbon dioxide stream from the carbon dioxide removal unit and the ammonia product stream from the second reactor to a third reactor to produce an urea product stream. In certain embodiments, the hydrocarbon feedstock is methane. In certain embodiments, the hydrocarbon feedstock is syngas.

In certain embodiments, the method further includes supplying air to the air separation unit to produce nitrogen and oxygen, wherein the nitrogen is supplied to the second reactor and the oxygen is supplied to the fuel cell unit. In certain embodiments, the method further includes supplying the high purity hydrogen stream from the first reactor to a first condenser to remove any trace water present in the high purity hydrogen stream.

In certain embodiments, the method further includes supplying air to a nitrogen separating unit to supply high purity nitrogen to the ammonia synthesis reactor and supply inert gas contaminated oxygen to the fuel cell with a higher concentration of oxygen than ambient air.

Numerous other aspects, features and benefits of the present disclosure may be made apparent from the following detailed description taken together with the drawing figures. The systems can include less components, more components, or different components depending on desired analysis goals. It should be further understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

DETAILED DESCRIPTION

Figure 1:
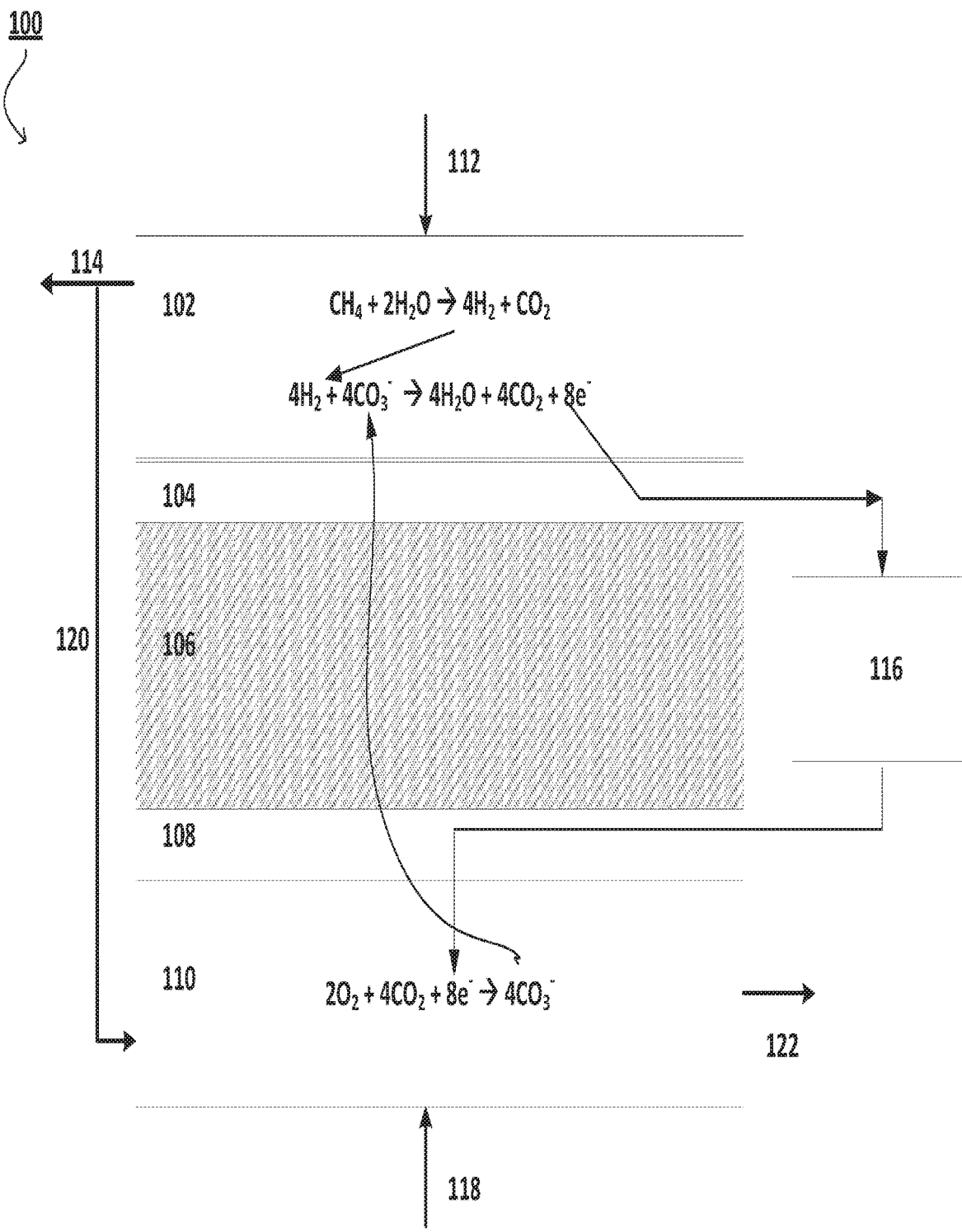
FIG. 1 shows an exemplary embodiment of a fuel cell unit modified to supply a hydrogen and carbon dioxide containing stream.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

The process described herein provides a polygeneration process for the combined production of ammonia, urea, and other hydrogen compounds from the products of a fuel cell. As used herein, "polygeneration" refers to an integrated process that has three or more outputs, which includes energy output(s), produced from one or more input resources. The fuel cell process generates a product stream consisting of core gases of carbon dioxide and hydrogen, which is then supplied to an ammonia and/or fertilizer production steps. In certain embodiments, the product stream is a hot gaseous stream. In certain embodiments, the gas stream can be supplemented with cold nitrogen, which has not been supplied to hot gas process, to produce nitrogen and ammonia-based fertilizer.

The present invention also provides a polygeneration method for the production of ammonia and/or nitrogen based fertilizers, such as urea and anhydrous ammonia from the byproduct gas of the fuel cell process, along with the concurrent production of energy. Extraction of 100% of the gas can result in no production of electricity.

In one aspect, the present invention provides a method for producing ammonia from products of the fuel cell process. The method includes the steps of supplying a hydrogen-containing feedstock, oxygen, and steam to a fuel cell process to generate product streams that includes carbon dioxide, hydrogen, heat, and electrons. In the presence of the anode, free electrons, generated by electrochemical reaction within the fuel cell, flow from the anode of the fuel cell into an electric circuit. The product stream gas is then supplied to a heat recovery unit to remove heat produced during the electrochemical reaction, then to a condenser to remove water and produce a gas stream comprising primarily hydrogen and carbon dioxide. The gas stream comprising primarily hydrogen and carbon dioxide from the first condenser is supplied to a carbon dioxide stripper to produce a hydrogen stream and a high purity carbon dioxide stream. The carbon dioxide stripper is charged with a solvent suitable for extracting carbon dioxide. The hydrogen stream can include carbon dioxide, carbon monoxide, carbon trioxide in transient form, and other fuel impurities. The hydrogen stream is supplied to a first reactor that includes a catalyst and is configured for the production of methane from the minor amounts of carbon dioxide present in the hydrogen stream. The product streams leaving the first reactor include a methane product stream and a high purity hydrogen stream.

Alternatively, to the methanator or in combination with it, the contaminated hydrogen stream can be sent to a pressure swing adsorption unit to purify the hydrogen and recycle or vent waste gas containing impurities removed from the hydrogen stream. The high purity hydrogen stream and nitrogen gas are supplied to a second reactor, said second reactor including a catalyst and being configured to produce an ammonia product stream. At this point, the process may be stopped to make ammonia and carbon dioxide; or the high purity carbon dioxide stream and ammonia are then supplied to a third reactor, said third reactor being configured to a product stream containing urea.

Disclosed herein are uses of fuel cells as consumers of hydrocarbon feedstock and sources of hydrogen for the production of hydrogen compounds. Examples of hydrocarbon feedstock used herein include natural gas, methane, and also synthetic gas produced from such sources as hydrocarbons, coal, or biomass. Fuel cells are essentially electrochemical devices that combine the gaseous feedstock with oxygen to produce electricity and heat, as well as water. In an embodiment, the oxygen is derived from the ambient air. In other embodiments, the oxygen can be supplied from an air separation unit or a nitrogen separation unit.

FIG. 1 is an illustration of an exemplary embodiment of a fuel cell unit 100 modified for the methods disclosed herein. Here, the fuel cell unit incorporate an anode chamber 102, an anode 104, a cathode 108, and a cathode chamber 110 with an electrolyte 106 in between the two. In this embodiment, the anode and the cathode are porous nickel (Ni) catalysts. The electrolyte 108 in this embodiment contains potassium and lithium carbonates. Fuel cells can contain different types of materials as anode, cathodes, electrolytes, and other catalysts, depending on the type and desired performance of the fuel cell. Examples of fuel cell systems include phosphoric acid fuel cells, solid oxide fuel cells, and polymer electrolyte membrane fuel cells.

Inlet stream 112 contains a mixture of hydrocarbon feedstock and steam that react at the anode chamber 102 to form hydrogen and $CO_2$. CH4 from the hydrocarbon feedstock is internally reformed to produce the product stream and the absence of combustion avoids the production of NOx and particulate pollutants. A portion of the gases, hydrogen and $CO_2$, are then consumed electrochemically in a reaction with carbonate electrolyte ions that produces water and electrons. A portion of the gases is also removed as product stream 114 to enter into an process for the production of hydrogen containing compounds, such as ammonia or urea. The electrons flow from the anode 104 through an external circuit to provide the power to the fuel cell load 116, and then return to be consumed in the electrochemical reaction at the cathode 108 and cathode chamber 110. The cathode 108 receives an incoming stream 118 containing oxygen. This oxygen can be supplied in the form of ambient air or as product streams from an air separation unit or from a nitrogen separation unit. $CO_2$ is recycled from the anode side via product stream 120. The oxygen supplied to the cathode, along with $CO_2$ recycled from the anode side, reacts with the electrons to produce carbonate ions that pass through the electrolyte to support the anode reaction. Excess oxygen and carbon dioxide is removed via stream 122.

Figure 2:
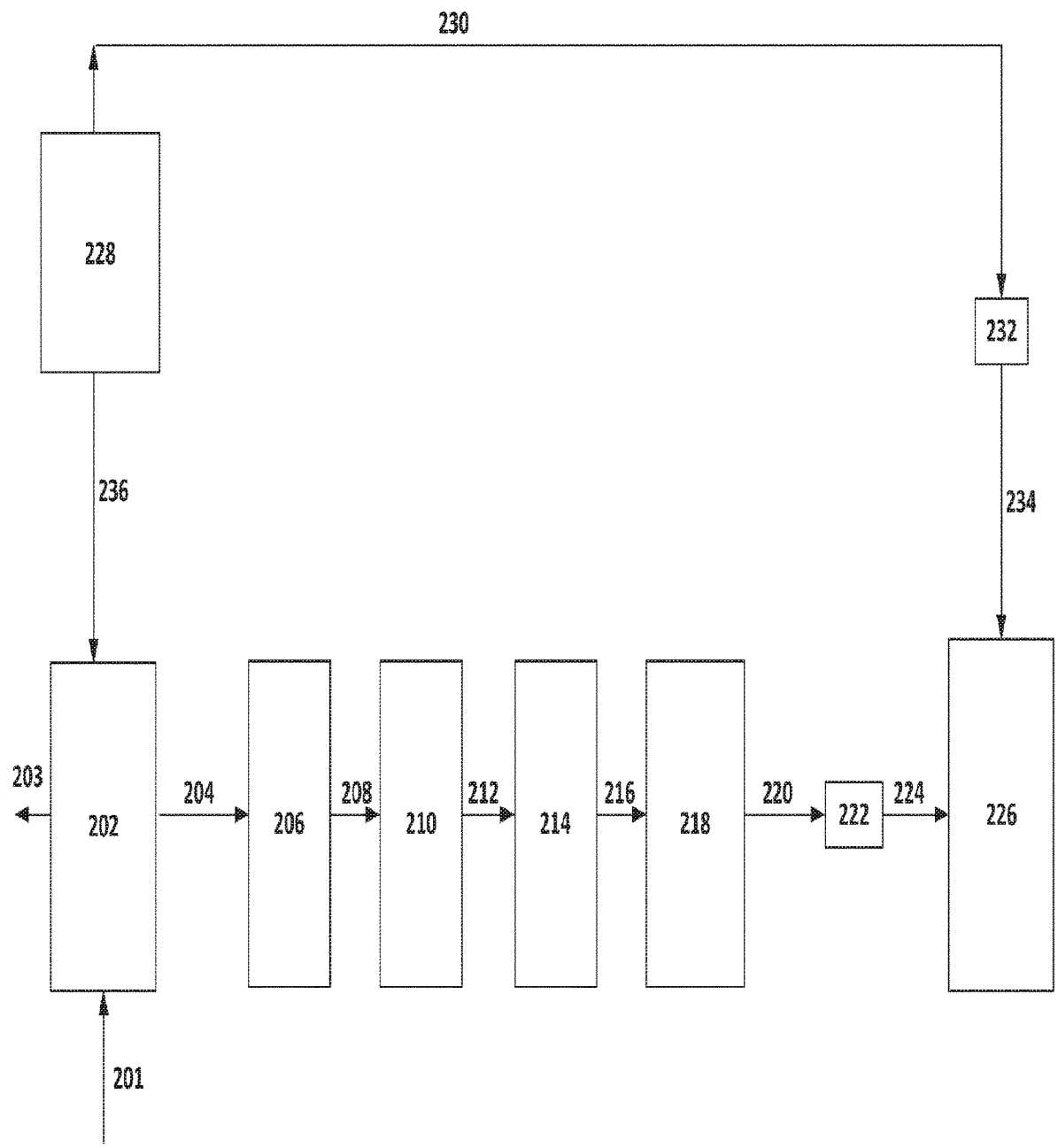
FIG. 2 is a block diagram of an exemplary method using a fuel cell unit for the production of ammonia, according to an embodiment.

FIG. 2 is an illustration of an exemplary embodiment of a fuel cell 202 modified for the methods disclosed herein. Inlet stream contains a mixture of hydrocarbon feedstock and steam and enters the fuel cell unit 202 via line 201. The hydrocarbon feedstock and steam react at the anode chamber of the fuel cell unit 202 to form hydrogen and $CO_2$. Gaseous product stream exiting fuel cell 202 via line 204 is at high temperature, typically at a temperature range between about 500 and 800° C., alternatively between about 600 and 780° C., alternatively about 700 and 760° C. Gaseous product stream via line 204 includes a mixture of hydrogen, carbon dioxide, oxygen, water (for example, as steam), and inert gases. In certain embodiments, the gas mixture can include between about 30 and 65 mol. % hydrogen, 15-32 mol. % carbon dioxide, and between 10 and 20 mol. % water and inert gases. In an alternate embodiment, the gas mixture can include between about 60 and 65 mol. % hydrogen, between 17 and 23 mol. % carbon dioxide, and between 10 and 15 mol. % water and inert gases. The exact ratio of the gaseous product stream depends on exact composition of the fuel source (i.e., methane, syngas, or other hydrocarbon source) and upon the stoichiometric balance of oxygen and fuel supplied to the fuel cell process.

Conversion of carbon to mostly carbonates and carbon dioxide and hydrogen to water is possible in a stoichiometric balance. In certain embodiments, a 4:1 ratio of hydrogen to carbon dioxide will be achieved at line 114. In certain embodiments, the process does not limit the ratio of carbon dioxide:hydrogen within these limits, but they are preferred for optimized production and efficiency. In certain embodiments, the fuel flow can control the production of carbon-oxides entering the system in stoichiometric balance or un-balance with if free oxygen enters the process.

Gaseous product stream in line 204 can optionally be supplied to heat exchanger 206 to control the temperature of the gases for further processes. When the fuel source is synthetic gas supplied, for example, by an integrated gasification cycle, carbon dioxide produced from the synthetic gas fuel as a byproduct can be injected into a carbon dioxide line, if the carbon dioxide is pure. If the carbon dioxide is not pure it could be injected into the gaseous product stream in line 204 and be subjected to further treatment for clean-up downstream. Heat exchanger 206 can be of any type known in the art, such as steam generator. The size of heat exchanger 206 can be selected based upon the cooling required to reduce the temperature of the gaseous product stream in line 204. For example, in certain embodiments, a first heat exchanger can be configured to reduce the temperature of the gaseous product stream in line 204 to less than about 240° F., alternatively less than about 190° F., or alternatively between about 175° F. and 215° F. Make up steam or water can be provided to the process via other lines, and can be supplied from an associated process. Excess steam from first heat exchanger can be used to drive an auxiliary turbine generator and/or an auxiliary compressor. Alternately, excess steam removed can be removed from the system to provide heating for an associated process.

Auxiliary turbine can be coupled to and drive compressor, which can be utilized for required gas compression loads. In certain embodiments, a motor-generator can be attached to the same compressor shaft and operate as a motor for start-ups and shutdowns. Steam supplied can be used to convert the motor to a generator as supply pressure overcomes the load of the compressor, unloading the motor, and eventually supplying enough torque to run both the compressor and motor as a compressor and generator. In certain embodiments, motor-generator can include slip rings and brushes or a permanent magnet generator for the field magnetism. In certain larger installations, multiple turbine units and motors can be used to meet redundancy requirements. Once redundancy requirement are met for start-up and shutdown reliability, a turbine-generator or turbine-compressor may be added to provide power generation or gas compression with excess steam. As is understood by one of skill in the art, not all turbine shafts will include motor-generator drives. The motor-generator drive advantageously facilitates the start-up and shutdown processes, and can reduce both the cost of the equipment and the number of shafts needed per piece of equipment. In certain embodiments, saturated steam can be removed from auxiliary turbine and supplied to a condenser, or to an associated process. Carbon dioxide can be supplied for compression by a compressor and supplied to the carbon dioxide removal process. Load control valves can be used to select the load of the compressor if needed and cycle the compressor into service mode, modulate mode, and out of service (unloaded). Some embodiments may not have need for the compressor if backpressure turbines and condensers are used and pressure is adequate to provide flow into carbon dioxide removal process directly.

The gas mixture exits via line 208 and can be supplied to condenser 210 to remove saturated water vapor. The water vapor condensed in condenser 210 is cooled by chilled water, which itself can be cooled by various means, such as with gases (e.g., nitrogen) provided by air separation unit 222 or outside cooling water. Condensate water removed from condenser 210 can be recycled to the fuel cell via the steam system for preheating.

Gas vapors exiting condenser 210 via line 212 through air separation baffles will primarily include a ratio of hydrogen and carbon dioxide, possibly also including small or trace amounts of contaminant and inert gases. In certain embodiments of the Haber-Bosch process, the gas ratio is about 74% hydrogen, 24% carbon dioxide, 2% other gases. Gas supplied via line 212 is supplied to carbon dioxide removal unit 214. In certain embodiments it may be necessary to have a vacuum pump or compressor present in carbon dioxide removal line 212 to extract gases from the condenser baffles and discharge to the carbon dioxide removal process 214 if a vacuum forms in the condenser 210 due to the collapse of the volume of steam to water. In backpressure type turbines if selected in the art to match the turbine design parameters, the carbon dioxide rich gas flow may not require the compressor to transfer gas from the condenser to the next stage of carbon dioxide removal process due to maintained positive pressure in the condenser. Carbon dioxide removal unit 214 removes carbon dioxide using an extraction media, such as an amine based solutions, such as MDEA (methyldiethanolamine), MEA (monoethanolamine), Ucarsol™, DGA (diglycolamine) and the like. In certain embodiments, carbon dioxide unit 214 can employ the Rectisol™ removal process. The carbon dioxide is then recovered in carbon dioxide recovery unit, which separates the amine based extraction media from the carbon dioxide. The carbon dioxide-lean amine based extraction media can then be recycled to carbon dioxide removal unit, which can cycle the extraction media in a rich and lean process loop. The amine can be condensed with chilled water from the chill water system, which exits from carbon dioxide recovery unit.

A high purity hydrogen stream is supplied to gas separation processes (for example, by pressure swing adsorption (PSA), condensation, membrane technologies, and the like). For example, the high purity hydrogen stream is supplied to pressure swing absorption unit 218 via line 216, or alternatively can be recovered or supplied to an alternate associated process (not shown). This hydrogen gas has a purity of greater than 95%, preferably at least about 99%, and includes uncaptured carbon dioxide and carbon monoxide, exiting the carbon dioxide stripper 214.

In certain embodiments, the highly pure hydrogen has a purity of at least about 99.9% exiting the pressure swing absorption unit 218 via line 220, and is supplied via line 220 to a compressor 222. Compressed highly pure hydrogen is then supplied via line 224 to a reactor 226 for the production of ammonia.

In certain embodiments, nitrogen is supplied from the air separation unit 228 via line 230 to a compressor 232. In certain embodiments, the compressors 222 and 232 may be the same compressor, Compressed nitrogen gas is supplied via line 234 to the reactor 226 for the production of ammonia. The air separation unit 228 also supplies the oxygen via line 236, or air for the fuel cell unit 202. In certain embodiments, the fuel cell process product stream can have a ratio of hydrogen:carbon dioxide of between about 2:1 and 4:1, alternatively between about 2.5:1 and 3.5:1. In certain embodiments the ratio is between about 2.9:1 and 3.1:1, alternatively about 3:1.

Reactor 226 includes a catalyst suitable for the production ammonia. In certain embodiments, the catalyst is an iron based catalyst, which can be promoted with potassium, calcium, and aluminum ($K_2O$, $CaO$ and $Al_2O_3$). In certain embodiments, the catalyst may be carbon fiber based matrix with of plating in palladium, ruthenium, nickel, rhodium, or combinations thereof. In certain embodiments, hydrogen and nitrogen are supplied to the reactor and passed over the catalyst to produce ammonia via the following reaction: $N_2 + 3H_2 \leftrightarrow 2NH_3$. In certain embodiments, make-up hydrogen gas can be supplied by other means (not shown), or when excess hydrogen is present, removed for sale or supply to an associated process (not shown). In certain embodiments, excess nitrogen can be vented or provided to an alternate process (not shown), or in certain embodiments, additional nitrogen can be added to the system (not shown) as needed.

Ammonia from reactor 226 can be supplied to other reactors for the preparation of urea, or extracted for collection or supply to an associated process. In certain embodiments, ammonia having a purity of at least about 99%, preferably at least about 99.9%, is combined with carbon dioxide having a purity of at least about 99%, preferably at least about 99.9%, supplied to produce urea by the following reaction: $2NH_3 + CO_2 \leftrightarrow NH_2COONH_4 \leftrightarrow NH_2CONH_2 + H_2O$. In the reaction for the production of urea, for each mole of urea that is formed, one mole of water is also produced. This water produced as a by-product of the urea synthesis, can be removed (not shown) and sold or supplied to an associated process. Urea product can be sent for collection or further processing, for example prilling and granulation.

Urea product is concentrated in three different methods in the art, by vacuum concentration, crystallization, or atmospheric evaporation. To prill, a concentrated urea solution called a "melt" is admitted to an evaporator to reduce moisture content. The resulting molten urea is pumped to spray nozzles of a tower and passed counter flow to air current. Prill is formed as urea droplets combine and fall through the tower and cool. Two primary processes are currently used in the art utilizing fluidized bed and non-fluidized bed prill towers. For granulation, molten urea is sprayed into a rotating drum or agitated pan having seed granules sieved from the output of the process. The rotation of the drum or agitation of the pan allows for product layering and coating, and for the combination with other products, such as clay, phosphates, or sulfur. The byproduct of both granulation and prilling is sieved for size and the small product is recycled to in the process. Granules of proper size are collected for storage and byproduct delivery.

In certain embodiments, a 3:1 ratio of hydrogen:carbon dioxide may be desirable for further separation of element gases to make urea ($NH_2CONH_2$). Certain design and fuel parameters of the fuel cell process may require a balanced stoichiometric ratio in the byproduct gas and therefore require supplemental hydrogen to be added to the ammonia making process, which is a precursor to making ammonia based fertilizer. By controlling the supplementing of certain components of the byproduct gases, it is possible to achieve the desired or necessary ratio of gases. Feedstock for the production of hydrogen can include recycled process water, condensate water from the ammonia and fertilizer production process, connate water, fresh water, saltwater, brine, desalinated water, deionized water, or deionized brine.

As noted above, in certain embodiments of the present invention, a major advantage of the inventions described herein is the replacement of the steam reformation process for the conversion of methane and synthesis gases to ammonia and/or nitrogen and ammonia based fertilizers. The use of fuel cell-based process provides a novel mechanism for the supply of hydrogen to this process. In certain embodiments, the system provides for the production of energy through fuel cell decomposition of the feedstock to carbon dioxide and water, and eliminates or significantly reduces the production of nitrous oxides prior to the production of nitrogen and ammonia based fertilizers. Advantageously, the energy produced can then sold to offset the cost of feedstock with net power sales. Additionally, the use of an air separation unit advantageously allows the cold exiting gases to be used as a heat sink in various associated heat exchangers and condensers. In certain embodiments, the apparatus and process described herein can include polygeneration looping for the production of additional power and heat. In certain embodiments, the process can include integration with known ammonia and fertilizer production processes to utilize the power generation by-products for the production of valuable chemical intermediates and products, such as sulfur, ammonia, nitrogen, hydrogen, noble gases, and rare earth metals. In certain embodiments, the feedstock for the process can be a fossil fuel or synthetic gas. In certain embodiments, the fossil fuel or synthetic gas can be treated to remove various contaminants, such as with gas separation equipment, baghouses, scrubbers, catalytic reactors, chemical treatment processes, and/or candle filters to achieve the desired output gases.

In certain embodiments, the apparatus and process described herein can reduce the mass flow of air to the fuel cell by employing the oxygen from the waste stream of air from a nitrogen separation unit, which increases oxygen by volume being supplied to the fuel cell process. In certain embodiments, the apparatus and process described herein can provide steam for steam turbine compression, desalination, combined heating and power generation, absorption chilling, and/or industrial and generation loads.

In certain embodiments, the apparatus and process described herein creates an ultra-low to zero-emission thermal power plant. In certain embodiments, other than start-up and shutdown venting, maintenance, equipment failure or trips, the process described herein provides no emissions from the thermal power plant. Put differently, in certain embodiments, during continuous operation the present process provides zero emissions in the generation of feedstock for power production and fertilizer.

In certain embodiments, the apparatus and process described herein reduces and repurposes industrial and greenhouse gases produced as a product of power generation into nitrogen containing chemical compounds, such as fertilizer. In certain embodiments, the apparatus and process described herein can be utilized for the production of various forms of fertilizer that incorporate ammonia and nitrogen. In certain embodiments, the apparatus and process described herein can be configured for urea production rather than ammonium-nitrate, thereby reducing the incidence of leaching of nitrates when applied as a fertilizer. In certain embodiments, the process can include a step wherein the prill is coated with sulfur, thereby providing a product having an increased disintegration time for the urea, and minimized nitrate leaching. In certain embodiments, sulfur can be removed from the feedstock and incorporated for sulfur treatment of the urea byproduct. Alternatively, in certain embodiments sulfur can be provided for sulfur treatment of the urea byproduct.

In certain embodiments, the steam and condensate produced in the associated processes, such as urea synthesis or feedstock industrial gasification to synthetic gas, can be used to provide heating or cooling, or can be used for purposes of providing pressurization. Steam production in excess of the steam generated from the feedstock to meet the process demands for the byproduct gas composition can be directed to auxiliary loads and used to generate additional power and either sold for a net increase of power sales, or can be supplied to power an associated process. Net steam produced by the auxiliary loads can be recycled in the steam loop or returned to the source of the steam. In certain embodiments, the use of cogeneration processes, such as the inclusion of solar thermal, geothermal, biomass, or waste heat can be integrated with the steam flow, as in the art. Though the use of heat exchangers and recycle streams, low temperature steam or water (i.e., having a temperature of between about 40 and 3000° C.) can be heated and/or pressurized beneficial levels through waste heat generated by other associated processes. Higher temperatures can be directed to the creation of steam, and then be sent through a turbine for power production, whereas medium and lower temperatures can generate heating or cooling effects in the thermodynamic cycle. In certain embodiments, chilled loads can be serviced through process looping between the power or industrial plant, ammonia processing, fertilizer processing, and/or granulation or prilling processes.

The sale of excess power produced, or internal use of excess power that is produced, will offset the power cost normally attributed to fertilizer production process and effectively reduce the cost of feedstock and fertilizer production costs. When steam reformation is used to produce the feedstock for ammonia based fertilizers, the feedstock of natural gas typically makes up about 70-90% of the total cost to produce the fertilizers.

In certain embodiments, air is supplied to the air separation unit and nitrogen is separated prior to the air injection process, such that pure or nearly pure oxygen is supplied to the oxidation step. As noted previously, the air supplied to the fuel cell process can have a purity of greater than 20%, alternatively greater than about 97%, alternatively greater than about 98%, alternatively greater than about 99%. In certain preferred embodiments, the oxygen can have a purity of greater than about 99.99%. By removing nitrogen from the oxygen prior the fuel cell process, the amount of energy and process equipment required to provide nitrogen in ammonia production is reduced while simultaneously increase concentration of oxygen to the fuel cell.

The latent heat of condensation provided by gases from the air separation cold box reduces water consumption requirements for evaporative cooling for heat loads such as steam turbines and heat exchangers. The elimination of air cooled condensers and cooling towers allows for the production of power as described herein in areas having low water resource and high ambient temperatures.

Known processes for the production of ammonia, such as the Haber-Bosch process, and known processes for the production of urea, such as the Stami or Uhde process, are exemplary processes that can be utilized in the present invention, using the byproduct gas from the fuel cell process to make nitrogen and ammonia based fertilizers. A variety of ammonia and fertilizer production processes could be advantageously utilized, thereby allowing for the use of a variable byproduct gas ratios to produce ammonia based products, such as ammonium-nitrate, ammonium sulfate, and ammonium phosphate.

Economic and efficient production of hydrogen can result in improved methods to produce ammonia based fertilizers through the Haber Bosch process or convert hydrogen into liquid hydrocarbons through the Fischer Tropsch process. Joining the fuel cell processes that isolates the hydrogen with processes that make new products, while capturing the heat of reaction or the release of energy in free electrons, and cogenerating steam or electricity with the Haber Bosch and Fisher Tropsch type cycles will optimize the efficiency of the overall process and reduce emissions.

In certain embodiments, the catalyst specifications will dictate adjustment of temperature, pressure, and gas ratio to meet the ideal conditions for the ammonia and fertilizer production process. For example, the process parameters will be different for the iron based catalyst, as compared with ruthenium and palladium catalysts Steam generators for heat recovery can be utilized and can provide the temperature and pressure balancing for the process gases, with the byproduct gas flowrate being selected based upon the power or steam demands. Water, gas and steam injection can also be used to control gas and density balances with controlled feedback loops. Process looping can provide mechanisms to recycle steam in the form of waste heat and condensate to the power generation or industrial process, and between the ammonia and fertilizer process. Heat sinks and sources provide efficiency loops to condense water, and to cool and reheat gases prior passing the gases over catalysts in the reaction zones. In certain embodiments, the chilled water that is used to cool various processes, such as for example for the removal of condensate, can receive primary cooling from nitrogen gas exiting the cold box of the air separation unit. The chilled water can be used for all chilled water requirements, and in certain embodiments can be supplemented with additional types of cooling or technologies.

In certain embodiments, ammonia can be produced by the Haber-Bosch process, wherein hydrogen and nitrogen gases are passed over an iron catalyst. Separation of hydrogen from the byproduct gas, concentration of the carbon-dioxide, removal of condensate, and temperature and pressure control can be performed prior to passing hydrogen over the iron catalyst and blending with nitrogen to form ammonia. Nitrogen separated by the air separation unit can be supplied directly to the ammonia production step In certain embodiments, excess nitrogen can be separated and sold. In one embodiment directed to the production of urea, compressed carbon dioxide is removed prior to the production of ammonia. The carbon dioxide can then be combined with the ammonia for synthesis of ammonium carbamate. Heat can be supplied from an associated process, such as urea process looping or auxiliary steam, can be used to strip excess carbon dioxide and ammonia from the ammonium carbamate. Two separate recycle loops can thus be formed; a first loop for the production of urea and water, and the second loop for the recycle of excess gases. Excess water can be removed, for example by evaporation, prior to the prilling or granulation process.

Exothermic reactions in the Urea processes described herein, and which produce steam and/or heat can discharge the steam to the heat recovery steam generator or auxiliary equipment. Reduced pressure and temperature steam can be returned for heat recovery.

Cooling in the ammonia and fertilizer production process can be done with condensate and chill water loops in the polygeneration process. Excess gases produced as a byproduct of the various reactions described herein can be recovered and sold. For example, nitrogen produced by air separation unit 228, and supplied to heat exchangers, can be used for cooling and for the production of ammonia. Excess nitrogen can be sold or can be vented. Inert gases can be stripped by air separation unit 228, such as argon, can be sold or vented, if below emission limits.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise. Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

We claim:

1. A method for the production of ammonia from byproduct gases of a fuel cell process, the method comprising the steps of:
    supplying a hydrocarbon feedstock and oxygen to a fuel cell unit to produce a first product stream containing gasses of carbon dioxide and hydrogen;
    supplying the gaseous product stream containing carbon dioxide and hydrogen from the fuel cell to a first condenser to remove water and produce a second product stream containing substantially pure hydrogen and carbon dioxide as compared to the first product stream;
    supplying the second product stream to a carbon dioxide stripper to produce a first high purity hydrogen stream and a carbon dioxide stream, the carbon dioxide stripper being charged with a solvent suitable for extracting carbon dioxide, and the first high purity hydrogen stream containing minor amounts of inert gases and carbon dioxide;
    supplying the first high purity hydrogen stream to a pressure swine adsorption unit to produce a second high purity hydrogen stream;
    supplying the second high purity hydrogen stream from the pressure swing adsorption unit and nitrogen gas from an air separation unit to a second reactor containing a second catalyst to produce an ammonia product stream.

2. The method of claim 1, further comprising supplying the carbon dioxide stream from the carbon dioxide removal unit and the ammonia product stream from the second reactor to a third reactor to produce an urea product stream.

3. The method of claim 1, wherein the hydrocarbon feedstock is comprises methane.

4. The method of claim 1, wherein the hydrocarbon feedstock is comprises syngas.

5. The method of claim 1, further comprising:
    supplying air to the air separation unit to produce nitrogen and oxygen, wherein the nitrogen is supplied to the second reactor and the oxygen is supplied to the fuel cell unit.

6. The method of claim 1, further comprising the step of supplying the second high purity hydrogen stream from the pressure swing adsorption unit to a second condenser to remove any trace water present in the high purity hydrogen stream.

* * * * *